United States Patent
Akao et al.

(10) Patent No.: US 7,676,337 B2
(45) Date of Patent: Mar. 9, 2010

(54) IRREVERSIBLE-REACTION MEASUREMENT METHOD

(75) Inventors: Kenichi Akao, Hachioji (JP); Seiichi Kashiwabara, Hachioji (JP); Toshiyuki Nagoshi, Hachioji (JP)

(73) Assignee: JASCO Corporation, Hachioji-shi, Tokyo (JP)

( * ) Notice: Subject to any disclaimer, the term of this patent is extended or adjusted under 35 U.S.C. 154(b) by 284 days.

(21) Appl. No.: 11/955,685

(22) Filed: Dec. 13, 2007

(65) Prior Publication Data
US 2008/0147331 A1 Jun. 19, 2008

(30) Foreign Application Priority Data
Dec. 15, 2006 (JP) ............... 2006-338436

(51) Int. Cl.
*G01R 23/16* (2006.01)
*G06F 11/00* (2006.01)

(52) U.S. Cl. .............. 702/77; 702/188; 702/189; 702/190; 356/451

(58) Field of Classification Search ............. 702/77–84, 702/187–190; 356/461
See application file for complete search history.

(56) References Cited

U.S. PATENT DOCUMENTS 5,838,438 A * 11/1998 Peale et al. ............... 356/451

7,224,464 B2 * 5/2007 Manning ................... 356/451

OTHER PUBLICATIONS

Japanese Patent Abstract Publication No. 61-176824 published Aug. 8, 1986, one page.
Japanese Patent Abstract Publication No. 2000-028434 published Jan. 28, 2000, 24 pages.
Japanese Patent Abstract Publication No. 07-151650 published Jun. 16, 1995, 12 pages.
Eguchi et al., "Position-Scanning Spectrophotometer As a Means of Observing Multicomponent Diffusion Phenomena in Liquid Phase," Journal of Chemical Engineering of Japan, vol. 17. No. 5, 1984, pp. 472-477.

* cited by examiner

*Primary Examiner*—Eliseo Ramos Feliciano
*Assistant Examiner*—Phuong Huynh
(74) *Attorney, Agent, or Firm*—Rankin, Hill & Clark LLP

(57) ABSTRACT

An irreversible-reaction measurement method comprising: a step in which a perturbation is applied to one of the divided portions of a measurement sample placed in a light path of a Fourier-transform spectrophotometer to cause an irreversible-reaction while a mirror of the spectrophotometer remains at a data point; a step in which interferogram is detected from the sample portion placed in the path at predetermined time intervals after the application of the perturbation; a step in which the mirror moves to and remains at the next data point after the reaction of the sample portion reaches an end point; a step in which the sample portion placed in the light path is changed to the next sample portion each time the mirror moves to the next data point; and a step in which the irreversible-reaction of the measurement sample is analyzed in accordance with the interferogram obtained by repeating the steps.

6 Claims, 9 Drawing Sheets

IRREVERSIBLE-REACTION MEASUREMENT METHOD

RELATED APPLICATIONS

The present application claims the benefits of priority of Japanese Patent Application No. 2006-338436, filed on Dec. 15, 2006, which is hereby incorporated by reference.

FIELD OF THE INVENTION

The present invention relates to irreversible-reaction measurement methods, and more specifically, to improvements made to their speedup technique.

BACKGROUND OF THE INVENTION

Changes in physical properties of measurement samples, such as liquid crystal, have been measured in the process in which the samples are relaxing from an applied perturbation, such as light and voltage.

Changes in physical properties accompanying a reaction in the measurement samples need to be measured quickly. When reproducible reversible reactions are measured, the step-scan method with a Fourier-transform spectrophotometer is generally used. Fast reversible reactions can also be measured as well by using the step-scan method with the Fourier-transform spectrophotometer (refer to Unexamined Japanese Patent Application Publication No. Sho-61-176824, for instance).

When irreversible reactions, which are isolated phenomena without reproducibility, are measured, the continuous-scan method is generally used. The continuous-scan method, however, cannot be used to measure reactions occurring faster than about 10 milliseconds due to the apparatus mechanism, and it has thus been difficult to measure fast irreversible reactions.

A faster apparatus could possibly be used, but such an apparatus has not yet been developed. Even if such an apparatus were available, it probably would not be adopted as a means for solving the problem because it would be very expensive.

The present inventors have found that the step-scan method is very effective in measuring irreversible reactions as well.

Use of the general step-scan method is limited theoretically to the measurement of reversible reactions. It has been difficult to apply the step-scan method to the measurement of irreversible reactions.

In the physical-property measurement field, there has been a demand for measuring faster irreversible reactions. However, because there has not been an appropriate technique for satisfying this demand and because the continuous-scan method has been used generally to measure irreversible reactions, measurable irreversible reactions have been limited to relatively slow ones.

SUMMARY OF THE INVENTION

In view of the problems of the related art described above, an object of the present invention is to provide an irreversible-reaction measurement method that allows faster irreversible reactions to be measured.

The present inventors have studied the measurement of irreversible reactions and have found that fast irreversible reactions can be measured not by measuring the irreversible reactions in the entire measurement sample simultaneously but by dividing the measurement sample into a plurality of parts, causing similar irreversible reactions in the divided parts, and rearranging data obtained through the measurement of the divided parts. With this finding, the inventors have made the present invention.

To achieve the object described above, the present invention provides an irreversible-reaction measurement method for measuring an irreversible reaction of a measurement sample, by using a step-scan measurement function of a Fourier-transform spectrophotometer, the measurement sample being divided into a plurality of parts depending on a desired number of measurement data points for the irreversible reaction and measurement thereof, the divided parts of the measurement sample being subjected to similar perturbations and producing similar irreversible reactions, the irreversible reactions in the divided parts of the measurement sample being measured in similar manners, and the irreversible-reaction measurement method including a perturbation-applying step, a detection step, a measurement-data-point setup step, a sample setup step, and a data processing step.

In the perturbation-applying step, a perturbation is applied to one of the divided parts of the measurement sample placed in a measurement light path of the Fourier-transform spectrophotometer to cause an irreversible reaction while a movable mirror of the Fourier-transform spectrophotometer remains at a measurement data point.

In the detection step, interferogram data is detected from the divided part of the measurement sample placed in the measurement light path at predetermined time intervals after the application of the perturbation.

In the measurement-data-point setup step, the movable mirror moves to and remains at the next measurement data point after the reaction of the divided part of the measurement sample placed in the measurement light path reaches an end point.

In the sample setup step, the divided part of the measurement sample placed in the measurement light path is changed to the next divided part of the measurement sample each time the movable mirror moves to the next measurement data point.

In the data processing step, the irreversible reaction of the measurement sample is analyzed in accordance with the interferogram data obtained by repeating the individual steps.

The irreversible reaction here means an isolated phenomenon without reproducibility.

Analysis performed in the present invention includes obtaining the information of an irreversible reaction by obtaining temporal changes in time-resolved spectrum data in accordance with interferogram data acquired by repeating individual steps or by obtaining temporal changes in light intensity at a specific wave number.

The Fourier-transform spectrophotometer used in the present invention includes a light source, a beam splitter, a fixed mirror, a movable mirror, and a detector, and a step-scan measurement function of the Fourier-transform spectrophotometer moves the movable mirror incrementally by a predetermined distance and, when the movable mirror stops, causes a detector to detect the interferogram data from the divided part of the measurement sample at each stop position of the movable mirror (each measurement data point).

The irreversible-reaction measurement method may be configured such that the measurement sample is placed on a table, the position of the divided part of the measurement sample in the measurement light path being moved by moving the table; in the perturbation-applying step, the irreversible reaction is caused by applying a perturbation to the divided part of the measurement sample placed in the measurement light path, among the plurality of divided parts of the measurement sample, which is placed on the table, while the movable mirror is remains at a measurement data point; in the sample setup step, the divided part of the measurement sample placed in the measurement light path is changed to the next divided part of the measurement sample by moving the table each time the movable mirror moves to the next measurement data point; and after the reaction of the divided part of the measurement sample placed in the measurement light path reaches the end point, the movable mirror moves to and remains at the next measurement data point, the table is moved to change the divided part of the measurement sample placed in the measurement light path to the next divided part of the measurement sample, a similar perturbation is applied to the next divided part of the measurement sample to cause a similar irreversible reaction, the interferogram data is detected from the next divided part of the measurement sample in a similar way, and this procedure is repeated.

The irreversible-reaction measurement method may be configured such that the measurement sample is different types of fluids that produce an irreversible reaction when they are mixed in a reaction cell by using a stopped-flow apparatus; the divided parts of the measurement sample are divided fluids formed by dividing the entire amounts of the different types of fluids into predetermined amounts and mixing them in the reaction cell by using the stopped-flow apparatus; in the perturbation-applying step, a perturbation is applied to the divided fluid by mixing the predetermined amounts of the different types of fluids by means of the stopped-flow apparatus each time the movable mirror moves to the next measurement data point; in the detection step, the Fourier-transform spectrophotometer is used to detect interferogram data from the divided fluid placed in the measurement light path in the reaction cell each time the movable mirror moves to the next measurement data point; in the sample setup step, the stopped-flow apparatus is used to replace the divided fluid in the reaction cell each time the movable mirror moves to the next measurement data point; and while the movable mirror remains at the measurement data point, the stopped-flow apparatus is used to mix the predetermined amounts of the different types of fluids, thereby producing the irreversible reaction in the divided fluid, the interferogram data is detected from the divided fluid, the movable mirror moves to and remains at the next measurement data point after the reaction of the divided fluid reaches the end point, the stopped-flow apparatus is used to replace the divided fluid in the reaction cell with the next divided fluid, thereby producing a similar irreversible reaction in the divided fluid, the interferogram data is detected in a similar way from the divided fluid, and this procedure is repeated.

The irreversible-reaction measurement method may be configured such that, in the detection step, the interferogram data is detected from the divided part of the measurement sample placed in the measurement light path by a multi-channel detector serving as a detector of the Fourier-transform spectrophotometer; and the interferogram data of each time period after the application of the perturbation is detected at the measurement data point by scanning the elements of the multi-channel detector successively at regular time intervals after the application of the perturbation to the divided part of the measurement sample while the movable mirror remains at the measurement data point.

Advantages Of The Invention

With the steps described above, the irreversible-reaction measurement method according to the present invention enables fast-irreversible-reaction measurement, which has heretofore been extremely difficult.

By combining the movement of the table and the step-scan method, the present invention allows a fast irreversible reaction to be measured.

According to the present invention, a combination of the stopped-flow apparatus and the step-scan method enables fast-irreversible-reaction measurement.

The present invention makes it possible to measure a fast irreversible reaction in a very short period by using a multi-channel detector of the Fourier-transform spectrophotometer to detect the interferogram data of each time period after the application of a perturbation.

DESCRIPTION OF THE PREFERRED EMBODIMENTS

Preferred embodiments of the present invention will be described below with reference to the drawings.

First Embodiment

Figure 1:
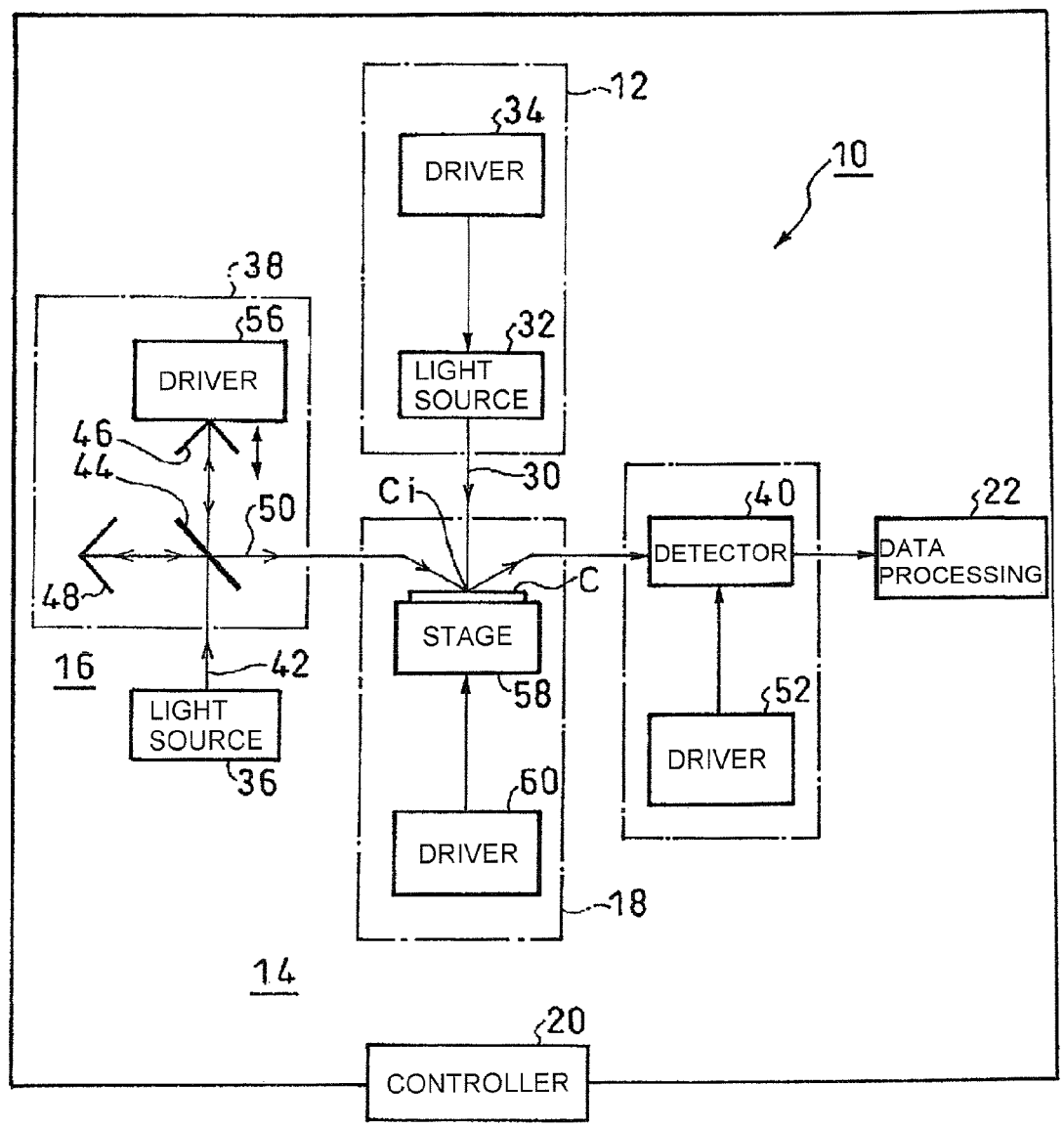
FIG. 1 is a diagram showing an outline structure of an apparatus for implementing an irreversible-reaction measurement method according to a first embodiment of the present invention.

FIG. 1 shows an outline structure of an irreversible-reaction measurement apparatus 10 for implementing an irreversible-reaction measurement method according to a first embodiment of the present invention.

The irreversible-reaction measurement apparatus 10 includes a perturbation-applying device 12, a Fourier-transform infrared spectrophotometer (Fourier-transform spectrophotometer) 14, which is used as a detector, a measurement-data-point setup device 16, a sample setup device 18, a controller 20, which is used as a repeating device, and a data processing device 22.

The perturbation-applying device 12 performs a perturbation-applying step of the present invention.

The Fourier-transform infrared spectrophotometer 14 performs a detection step of the present invention.

The measurement-data-point setup device 16 performs a measurement-data-point setup step of the present invention.

The sample setup device 18 performs a sample setup step of the present invention.

The controller 20 repeats the steps of the present invention until desired measurement is completed.

The data processing device 22 performs a data processing step of the present invention.

In the present invention, the measurement sample produces an irreversible reaction, which is an isolated phenomenon without reproducibility. The measurement sample in the first embodiment is divided into the plurality of parts depending on a desired number of measurement data points, and the irreversible reactions produced there are measured. More specifically, in the first embodiment, the divided parts of the measurement sample produce similar irreversible reactions under similar perturbations, and the irreversible reactions in those divided parts of the measurement sample are measured in similar ways.

In the first embodiment, each time a movable mirror of the Fourier-transform infrared spectrophotometer 14 moves to the next measurement data point, a table moves to bring the next divided part of the measurement sample into the measurement light path of the Fourier-transform infrared spectrophotometer 14, and the irreversible reaction there is measured.

The components will be described below in detail.

<Perturbation-Applying Device>

The perturbation-applying device 12 includes a perturbation light source 32 such as a pulsed laser for producing a perturbation 30, such as a short light pulse, and a perturbation driver 34 for driving the perturbation light source 32.

In the first embodiment, the controller 20 controls the operation of the perturbation driver 34, which drives the perturbation light source 32.

<Detector>

The Fourier-transform infrared spectrophotometer 14, used as a detector in the first embodiment, includes an infrared light source 36, an interferometer 38, a multi-channel detector 40, and the data processing device 22.

The infrared light source 36 emits infrared light 42.

The interferometer 38 includes a beam splitter 44, a movable mirror 46, and a fixed mirror 48. The interferometer 38 generates interference light 50 from the infrared light 42 emitted from the infrared light source 36 and sends the interference light 50 onto a divided part $C_i$ placed in a measurement light path 54, among a plurality of divided parts $C_1$ to $C_m$ of the measurement sample C.

In the first embodiment, while the movable mirror 46 remains at a measurement data point, a detector driver 52 successively scans individual elements of the multi-channel detector 40 at regular time intervals after application of the perturbation 30 to the divided part $C_i$ of the measurement sample C to detect interferogram data in the corresponding time periods after the application of the perturbation 30.

The data processing device 22 Fourier-transforms the interferogram data coming from the multi-channel detector 40 and provides spectrum data.

In the first embodiment, the controller 20 controls the step-scan measurement function of the Fourier-transform infrared spectrophotometer 14.

<Measurement-Data-Point Setup Device>

The measurement-data-point setup device 16 includes the movable mirror 46 and a movable-mirror driver 56, for instance.

In the first embodiment, the controller 20 controls the operation of the movable-mirror driver 56 to move the movable mirror 46 to the next measurement data point and stop it there after the reaction in the divided part $C_i$ of the measurement sample C placed in the measurement light path of the Fourier-transform infrared spectrophotometer reaches the end point.

<Sample Setup Device>

The sample setup device 18 includes a table 58 and a table driver 60.

The table 58 carries the measurement sample C and can move the sample C freely in X and Y directions parallel to the measurement plane.

The table driver 60 drives the table 58 in the X and Y directions.

In the first embodiment, each time the movable mirror 46 moves to the next measurement data point, the controller 20 controls the operation of the table driver 60 to change the target position from the divided part $C_i$ of the measurement sample C on the table 58 to the next divided part $C_{i+1}$ of the measurement sample C.

<Repeater>

The controller 20 controls the operation of the perturbation-applying device 12, the Fourier-transform infrared spectrophotometer 14, the measurement-data-point setup device 16, and the sample setup device 18 to repeat the corresponding steps until desired measurement is completed.

<Data Processing Device>

The data processing device 22 is formed of a computer, for instance. The data processing device 22 analyzes the irreversible reactions of the measurement sample C in accordance with the interferogram data of the divided parts $C_1$ to $C_m$ of the measurement sample C obtained by repeating the corresponding steps of the first embodiment.

The irreversible-reaction measurement apparatus 10 for implementing the irreversible-reaction measurement method of the first embodiment is structured generally as described above and works as described below.

One of the features of the present invention is the capability of measuring a fast irreversible reaction, which has been very difficult before. In the present invention, the whole measurement sample C does not produce an irreversible reaction at a time. The measurement sample C is divided into the plurality of parts $C_1$ to $C_m$ in which similar irreversible reactions occur, and those divided parts of the measurement sample C are used to produce and measure the irreversible reactions.

In the first embodiment, the measurement sample C is placed on the table 58. Each time the movable mirror 46 of the Fourier-transform infrared spectrophotometer 14 moves to the next measurement data point, the table 58 moves to change the divided part $C_i$ of the measurement sample C placed in the measurement light path of the Fourier-transform infrared spectrophotometer 14, and the irreversible reactions are produced and measured similarly in the divided parts $C_1$ to $C_m$ of the measurement sample C.

Figure 2:
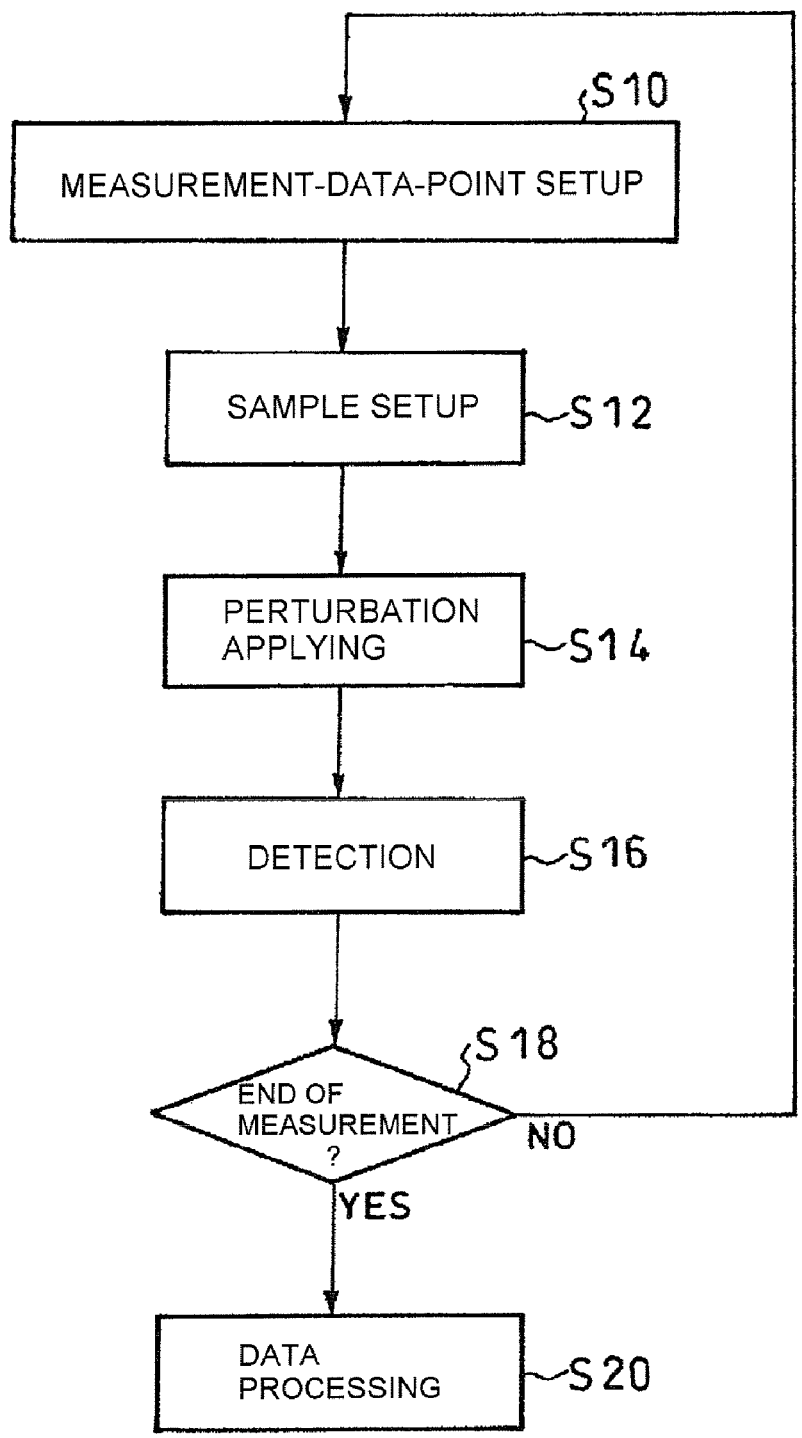
FIG. 2 is a flow chart showing the procedure of the irreversible-reaction measurement method according to the first embodiment of the present invention.

The first embodiment includes a measurement-data-point setup step S10, a sample setup step S12, a perturbation-applying step S14, a detection step S16, a repetition step S18, and a data processing step S20, as shown in FIG. 2.

In the measurement-data-point setup step S10, the movable mirror 46 moves to a predetermined measurement data point and remains there.

In the sample setup step S12, the table 58 moves to bring a predetermined divided part of the measurement sample C into the measurement light path.

In the perturbation-applying step S14, while the movable mirror 46 remains at the measurement data point, a perturbation, such as a short light pulse, is applied to the measurement sample on the table 58 to cause an irreversible reaction in the divided part of the measurement sample C placed in the measurement light path.

In the detection step S16, the Fourier-transform infrared spectrophotometer 14 detects the interferogram data from the divided parts each in the measurement light path at the time intervals after application of the perturbation.

The repetition step S18 causes the measurement-data-point setup step S10, the sample setup step S12, the perturbation-applying step S14, and the detection step S16 to be repeated until the desired measurement is completed.

In the measurement-data-point setup step S10, after the reaction in the divided part of the measurement sample C placed in the measurement light path reaches the end point, the movable mirror 46 moves to the next measurement data point and remains there.

In the sample setup step S12, each time the movable mirror 46 moves to the next measurement data point, the table 58 moves to change the target position in the measurement light path from the current divided part to the next divided part.

Then, in the first embodiment, the perturbation-applying step S14 and the detection step S16 are performed in that order.

If it is found in the repetition step S18 that the desired measurement has been completed, the data processing step S20 is performed.

In the data processing step S20, the irreversible reactions of the measurement sample are analyzed in accordance with the interferogram data obtained by repeating the corresponding steps.

In the first embodiment, changes in physical properties accompanying the irreversible reaction caused by the application of the perturbation 30 to the measurement sample C are measured by dividing the sample C into the plurality of parts $C_1$ to $C_m$ and by causing and measuring similar irreversible reactions in those parts, as shown in FIG. 3. Accordingly, a combination of the table moving device and the step-scan method is used.

Figure 3A:
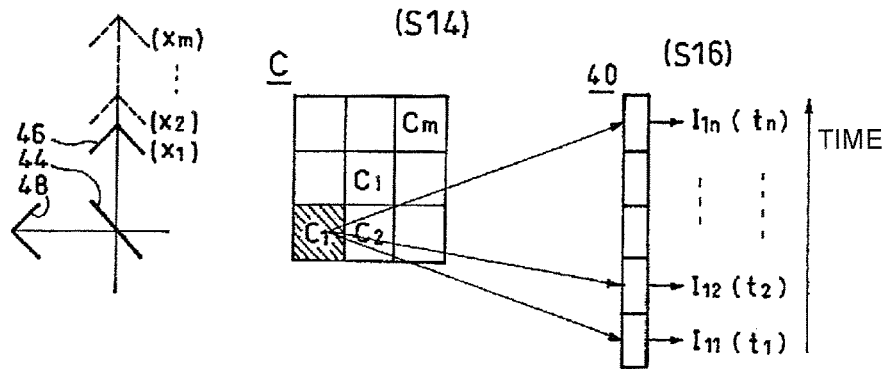
FIGS. 3A to 3C are diagrams illustrating individual steps in the irreversible-reaction measurement method according to the first embodiment of the present invention.
Figure 3B:
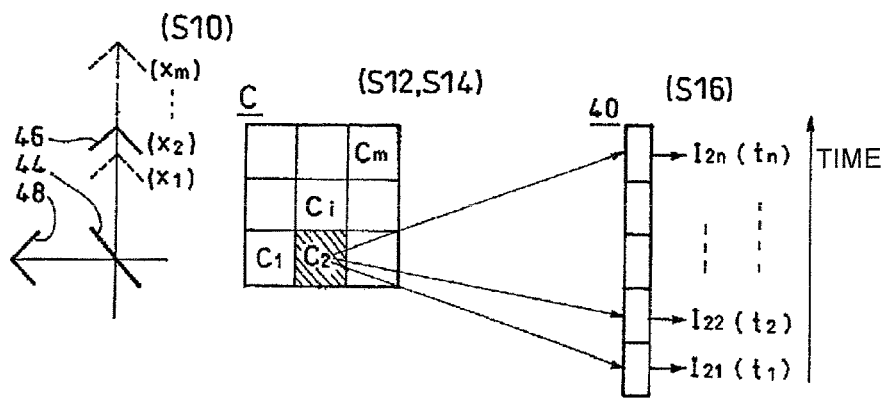
Figure 3C:
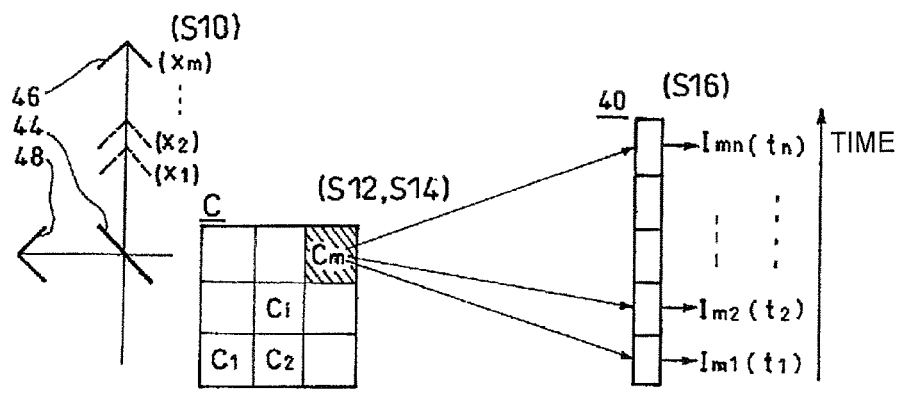

FIG. 3A is a diagram illustrating the steps at a measurement data point $x_i$; FIG. 3B is a diagram illustrating the steps at a measurement data point $x_2$; FIG. 3C is a diagram illustrating the steps at a measurement data point $x_m$.

As shown in FIG. 3A, while the movable mirror 46 remains at the measurement data point $x_1$, the perturbation-applying step S14 and the detection step S16 are performed at the divided part $C_1$ of the measurement sample C placed in the measurement light path. In the detection step S16, the elements of the multi-channel detector 40 are scanned at the regular time intervals after the application of the perturbation to the part $C_1$ of the measurement sample C, and the interferogram data $I_{11}$ to $I_{1n}$ at the measurement data point $x_1$ in the time periods $t_1$ to $t_n$ after the application of the perturbation can be detected.

In the first embodiment, after the reaction in the divided part $C_1$ of the measurement sample C reaches the end point, the movable mirror 46 moves to the next measurement data point $x_2$ and remains there as shown in FIG. 3B. Then, the table 58 moves to change the target position in the measurement light path to the next divided part $C_2$ of the measurement sample C, and the perturbation-applying step S14 and the detection step S16 are performed similarly at the divided part $C_2$ of the measurement sample C.

These steps are repeated until the desired measurement is completed, or until the interferogram data at the measurement data point $x_m$, as shown in FIG. 3C, is obtained.

In accordance with the interferogram data at the measurement points, the interferogram data of the measurement sample C is obtained, and thus fast irreversible reactions can be measured.

For example, the interferogram data of the measurement sample C is obtained in accordance with the interferogram data $I_{11}$ to $I_{1n}$ of delay time periods $t_1$ to $t_n$ at the measurement data point $x_1$ obtained from the divided part $C_1$ of the measurement sample C, the interferogram data $I_{21}$ to $I_{2n}$ of delay time periods $t_1$ to $t_n$ at the next measurement data point $x_2$ obtained from the divided part $C_2$ of the measurement sample C, through the interferogram data $I_{m1}$ to $I_{mn}$ of delay time periods $t_1$ to $t_n$ at the measurement data point $x_m$ obtained from the divided part $C_m$ of the measurement sample C.

In the first embodiment, the fast irreversible reaction of the measurement sample C can be analyzed by obtaining temporal changes in the time-resolved spectrum in accordance with the interferogram data of the measurement sample C. The fast irreversible reaction of the measurement sample C can be analyzed in further detail by obtaining temporal changes in light intensity at a specific wave number in accordance with the temporal changes in the time-resolved spectrum.

Since the multi-channel detector 40 is used as the detector of the Fourier-transform infrared spectrophotometer 14 in the first embodiment, the measurement time is reduced.

In the first embodiment, while the movable mirror 46 remains at a measurement data point, the elements of the multi-channel detector 40 are successively scanned at the regular time intervals after the application of the perturbation 30 to the divided part $C_i$ of the measurement sample C placed in the measurement light path to detect the interferogram data in the individual time periods after the application of the perturbation 30. Therefore, in the first embodiment, the measurement time is reduced in comparison with when the interferogram data is detected by a single detector in a specific time period after application of the perturbation.

Since the state after application of the perturbation varies moment by moment, it is advantageous to use the multi-channel detector 40 as the detector of the Fourier-transform infrared spectrophotometer 14 in the first embodiment, where those changes must be measured.

Second Embodiment

The first embodiment described above uses the combination of the movement of the table and the step-scan method to measure the fast irreversible reaction, but the present invention is not limited to this combination. A combination of a stopped-flow apparatus and the step-scan method is also possible, as described below.

Figure 4:
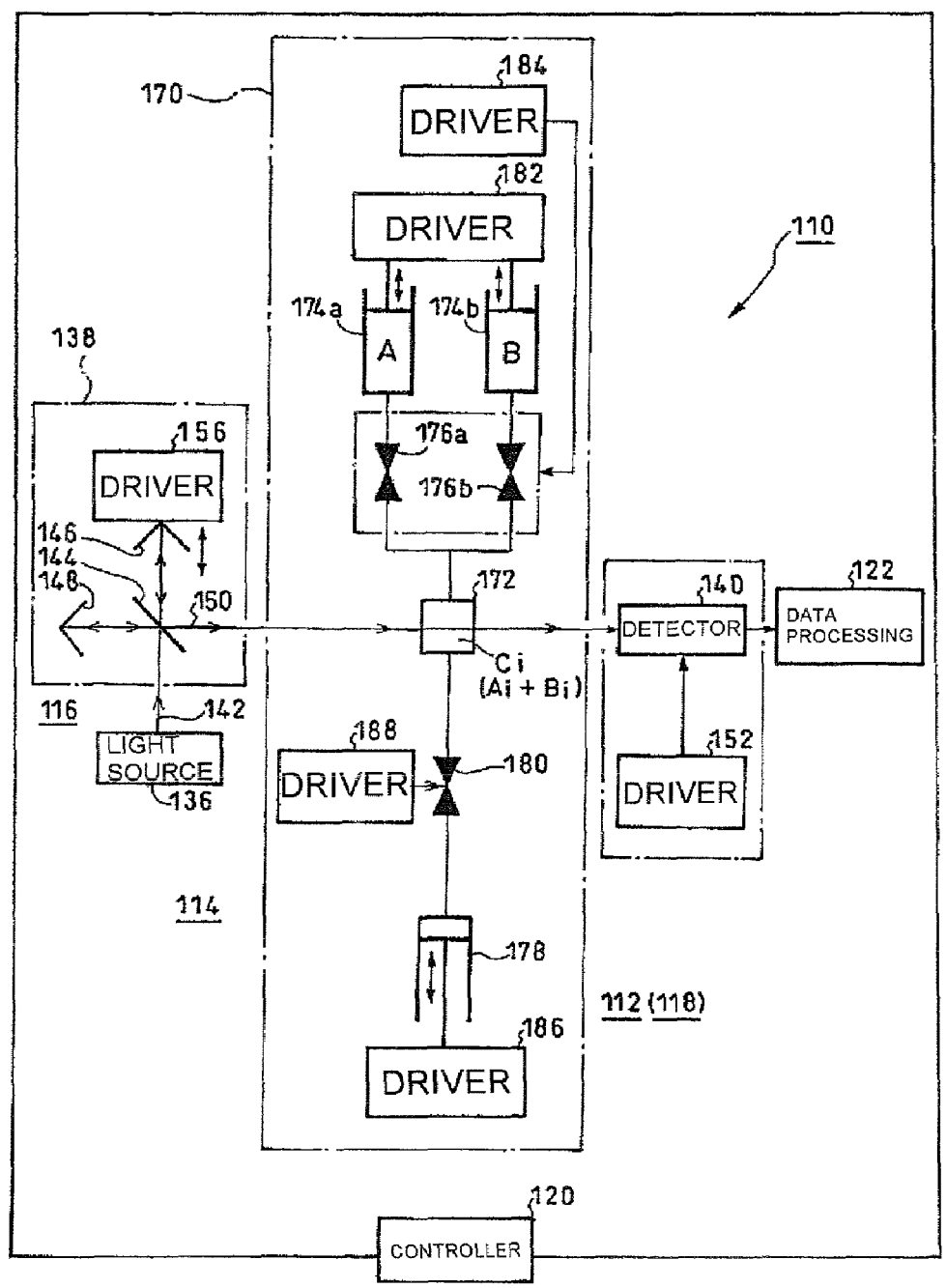
FIG. 4 is a diagram showing an outline structure of an apparatus for implementing an irreversible-reaction measurement method according to a second embodiment of the present invention.

FIG. 4 shows an outline structure of an irreversible-reaction measurement apparatus 110 for implementing an irreversible-reaction measurement method according to a second embodiment of the present invention. Elements corresponding to the elements in the first embodiment will be denoted by reference numerals obtained by adding 100 to the numerals used in the first embodiment, and a description of those elements will be omitted.

The second embodiment assumes that the measurement sample C is a mixture of a plurality of liquids. Each time a movable mirror 146 moves to the next measurement data point, a divided liquid mixture (divided part, divided fluid) $C_i$ in a reaction cell 172 is replaced by a stopped-flow apparatus 170, and an irreversible reaction of the divided liquid mixture $C_i$ in the reaction cell 172 is measured.

In a perturbation-applying step S114 of the second embodiment, the stopped-flow apparatus 170 is used to mix predetermined amounts of divided sample liquids $A_i$ and $B_i$ in the reaction cell 172, thereby applying a perturbation to the divided liquid mixture $C_i$ of the divided sample liquids $A_i$ and $B_i$.

In a detection step S116 of the second embodiment, a Fourier-transform infrared spectrophotometer 114 detects interferogram data from the divided liquid mixture $C_i$ in the reaction cell 172.

In a sample setup step S112 of the second embodiment, each time the movable mirror 146 moves to the next measurement data point, the stopped-flow apparatus 170 replaces the divided liquid mixture $C_i$ in the reaction cell 172.

Therefore, in the second embodiment, the stopped-flow apparatus 170 is disposed in the sample chamber of the Fourier-transform infrared spectrophotometer 114.

The stopped-flow apparatus 170 includes supply syringes 174a and 174b, supply valves 176a and 176b, the reaction cell 172, a discharge syringe 178, a discharge valve 180, a supply syringe driver 182, a supply valve driver 184, a discharge syringe driver 186, and a discharge valve driver 188.

The supply syringes 174a and 174b are provided upstream of the reaction cell 172 and contain sample liquids A and B. The supply syringes 174a and 174b are driven by the supply syringe driver 182 to send the predetermined amounts of divided sample liquids $A_i$ and $B_i$ of the sample liquids A and B, to the downstream reaction cell 172.

The supply valves 176a and 176b are disposed between the supply syringes 174a and 174b and the reaction cell 172. The supply valves 176a and 176b are opened and closed by the supply valve driver 184.

The reaction cell 172 is placed in the measurement light path of the Fourier-transform infrared spectrophotometer 114. In the reaction cell 172, the divided sample liquids $A_i$ and $B_i$ are mixed, and the mixture of the divided sample liquids $A_i$ and $B_i$ causes an irreversible reaction to occur in the divided liquid mixture $C_i$.

The discharge syringe 178 is disposed downstream of the reaction cell 172 and discharges the divided liquid mixture $C_i$ from the reaction cell 172.

The discharge valve 180 is disposed between the reaction cell 172 and the discharge syringe 178. The discharge valve 180 is opened and closed by the discharge valve driver 188.

A controller 120 controls the operation of the supply syringe driver 182, the supply valve driver 184, the discharge syringe driver 186, and the discharge valve driver 188 appropriately when the divided liquid mixture $C_i$ is supplied into the reaction cell 172, when interferogram data is detected from the divided liquid mixture $C_i$ in the reaction cell 172, and when the divided liquid mixture $C_i$ is discharged from the reaction cell 172.

The irreversible-reaction measurement apparatus 110 for implementing the irreversible-reaction measurement method of the second embodiment is structured generally as described above and works as described below.

In the second embodiment, a combination of the stopped-flow apparatus 170 and the step-scan method is used to measure changes in physical properties accompanying an irreversible reaction in the divided liquid mixture $C_i$ of the divided sample liquids $A_i$ and $B_i$.

The measurement sample in the second embodiment is the liquid mixture C of two different sample liquids A and B, which produce irreversible reactions when mixed in the reaction cell 172 by the stopped-flow apparatus 170. The stopped-flow apparatus 170 mixes the predetermined amounts of sample liquids A and B in the reaction cell 172.

Figure 5:
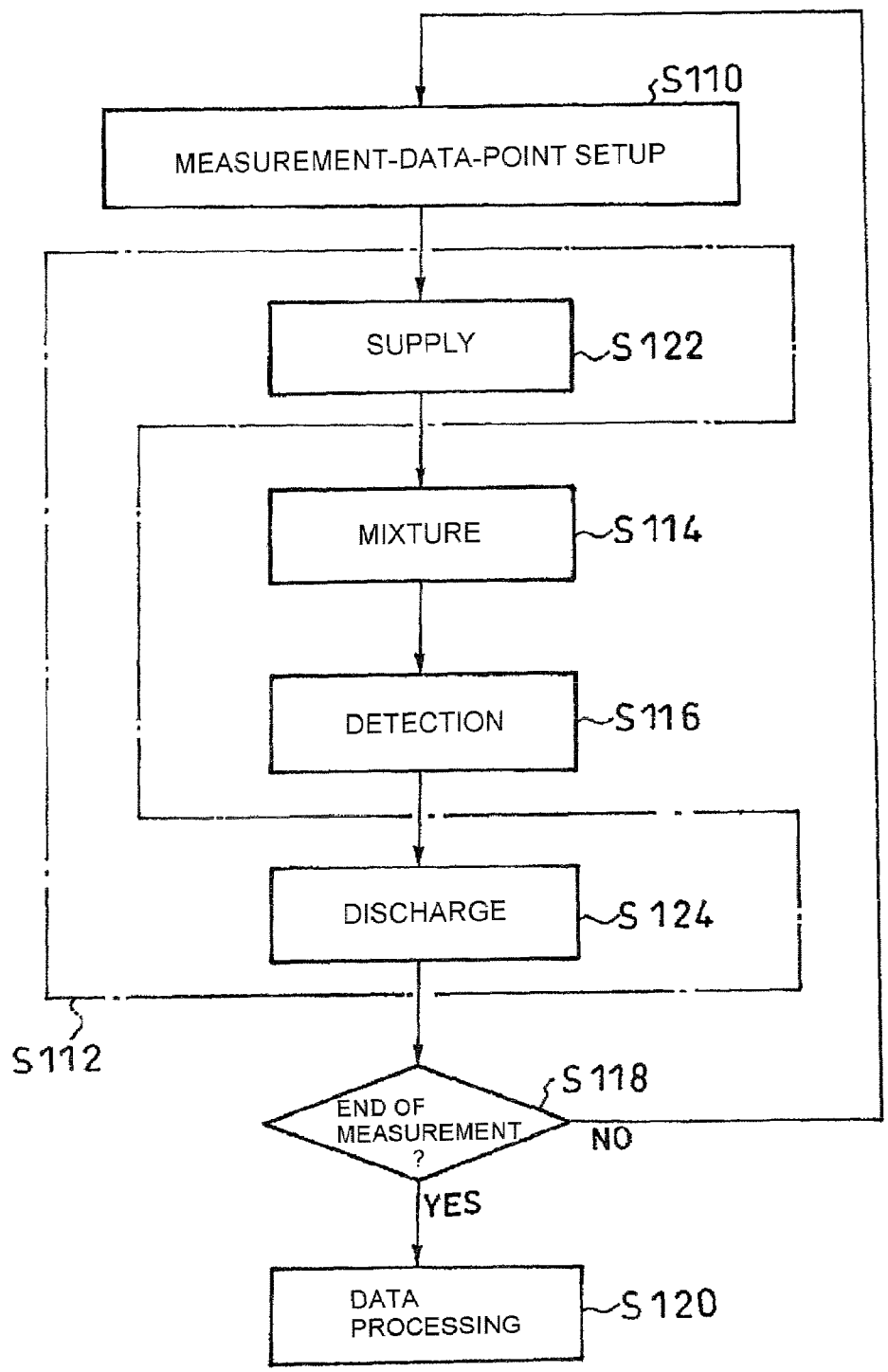
FIG. 5 is a flow chart showing the procedure of the irreversible-reaction measurement method according to the second embodiment of the present invention.

In the perturbation-applying step S114 of the second embodiment, shown in FIG. 5, each time the movable mirror 146 moves to the next stop position, the stopped-flow apparatus 170 mixes the divided sample liquids $A_i$ and $B_i$ in the reaction cell 172 to produce the divided liquid mixture $C_i$ and applies a perturbation to the divided liquid mixture $C_i$ in the reaction cell 172.

In the detection step S116 of the second embodiment, each time the movable mirror 146 moves to the next measurement data point, the Fourier-transform infrared spectrophotometer 114 detects the interferogram data from the divided liquid mixture $C_i$ in the reaction cell 172.

In the sample setup step S112 of the second embodiment, each time the movable mirror 146 moves to the next measurement data point, the stopped-flow apparatus 170 replaces the divided liquid mixture $C_i$ in the reaction cell 172. For that purpose, the sample setup step S112 in the second embodiment includes a supply step S122 and a discharge step S124.

In the supply step S122, the divided sample liquids $A_i$ and $B_i$ are supplied into the reaction cell 172, thus providing the divided liquid mixture $C_i$.

In the discharge step S124, the divided liquid mixture $C_i$ is discharged from the reaction cell 172.

In the second embodiment, the stopped-flow apparatus 170 replaces the divided liquid mixture in the reaction cell 172 by supplying the divided liquid mixture $C_i$ into the reaction cell 172 and discharging the divided liquid mixture $C_i$ from the reaction cell 172 and by supplying the next divided liquid mixture $C_{i+1}$ into the reaction cell 172 and discharging the divided liquid mixture $C_{i+1}$ from the reaction cell 172.

In the second embodiment, the irreversible reaction is caused not by mixing the whole amounts of the sample liquids A and B at a time but by using the predetermined amounts of the liquids in accordance with the number of measurement data points. Each time the movable mirror 146 moves to the next measurement data point, the stopped-flow apparatus 170 replaces the divided liquid mixture in the reaction cell 172, and the irreversible reaction of the divided liquid mixture is measured.

A data processing device 122 rearranges the interferogram data of the liquid mixture in accordance with the interferogram data obtained from the divided liquid mixtures as described above, in the same way as described in the first embodiment. The irreversible reaction of the liquid mixture is analyzed in accordance with the interferogram data of the liquid mixture.

The individual steps will be described in further detail.

In the second embodiment, as shown in FIG. 6, the whole amounts of the sample liquids A and B are not mixed at a time. As shown in FIG. 6A, for instance, the sample liquid A is used in the predetermined amounts of divided sample liquids $A_1$ to $A_m$, and the sample liquid B is used in the predetermined amounts of divided sample liquids $B_1$ to $B_m$. As a result, the liquid mixture in the reaction cell 172 is not given at one time but is given as the divided liquid mixture $C_i$ in predetermined amounts.

<Supply>

Figure 6A:
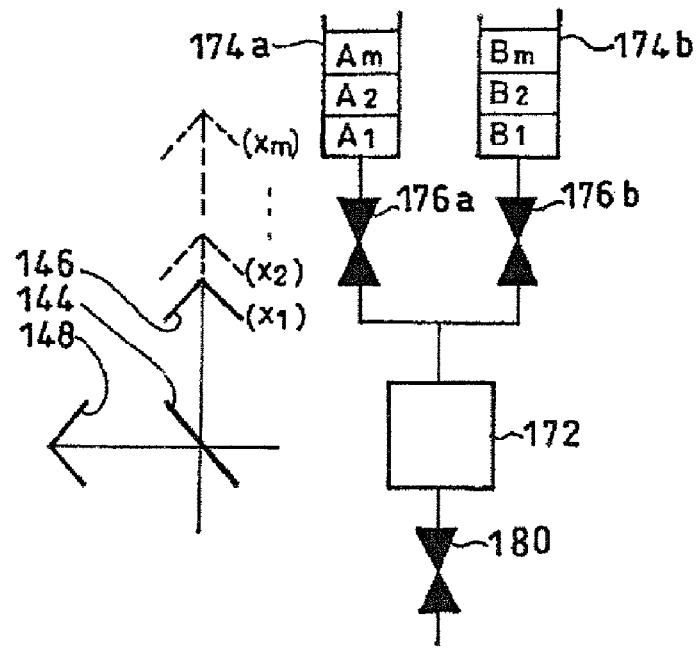
FIG. 6A is a diagram illustrating a step in the irreversible-reaction measurement method according to the second embodiment of the present invention.
Figure 6B:
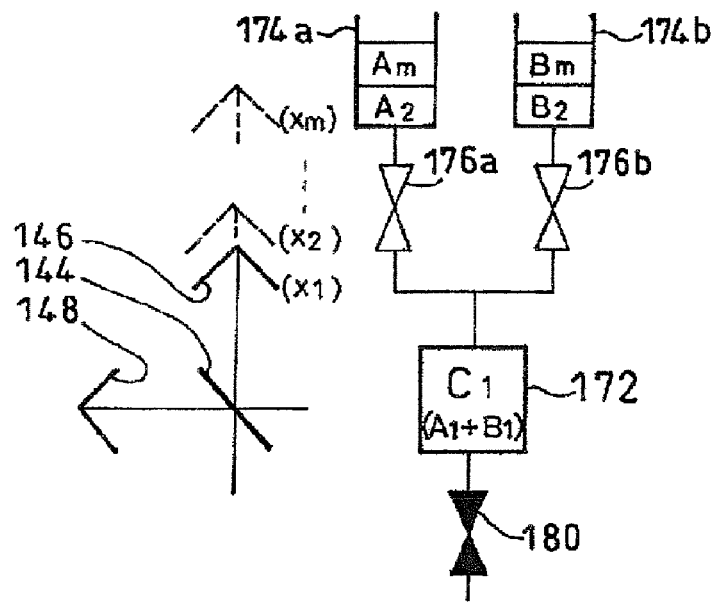
FIG. 6B is a diagram illustrating another step in the irreversible-reaction measurement method according to the second embodiment of the present invention.

As shown in FIG. 6B, while the movable mirror 146 remains at a measurement data point $x_1$, the stopped-flow apparatus 170 starts supplying the divided sample liquids $A_1$ and $B_1$ rapidly from the supply syringes 174a and 174b to the reaction cell 172. At that moment, the supply valves 176a and 176b are opened, and the discharge valve 180 is closed.

Figure 6C:
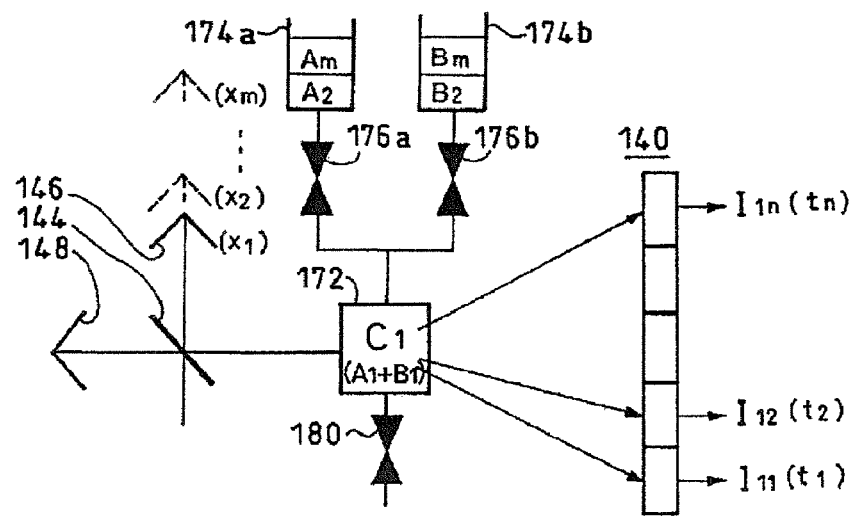
FIG. 6C is a diagram illustrating another step in the irreversible-reaction measurement method according to the second embodiment of the present invention.

After the divided sample liquids $A_1$ and $B_1$ supplied from the supply syringes 174a and 174b are mixed in the reaction cell 172, the liquid supply is stopped, as shown in FIG. 6C. At that moment, the supply valves 176a and 176b and the discharge valve 180 are closed.

<Perturbation Application>

When the divided sample liquids $A_1$ and $B_1$ supplied from the supply syringes 174a and 17b are mixed in the reaction cell 172, an irreversible reaction occurs in the divided liquid mixture $C_1$ in the reaction cell 172, and the interferogram data accompanying the reaction in the divided liquid mixture $C_i$ occurring in the reaction cell 172 is detected.

<Discharge>

Figure 6D:
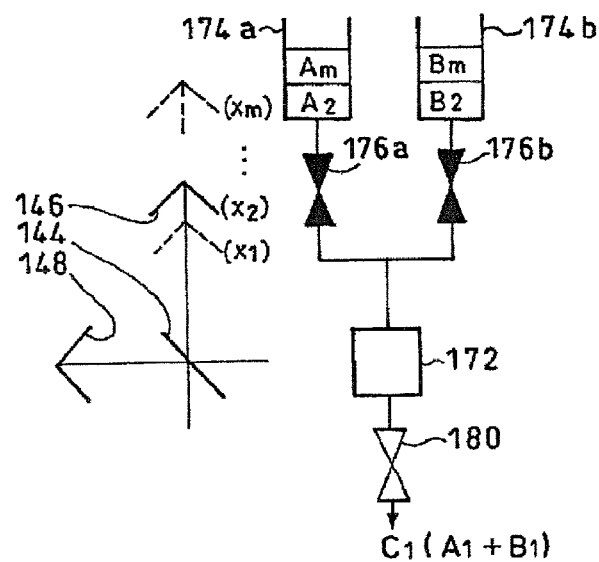
FIG. 6D is a diagram illustrating another step in the irreversible-reaction measurement method according to the second embodiment of the present invention.

After the irreversible reaction of the divided liquid mixture $C_1$ in the reaction cell 172 reaches the end point, the stopped-flow apparatus 170 discharges the divided liquid mixture $C_1$ from the reaction cell 172, as shown in FIG. 6D. At that moment, the supply valves 176a and 176b are closed, and the discharge valve 180 is opened.

Figure 6E:
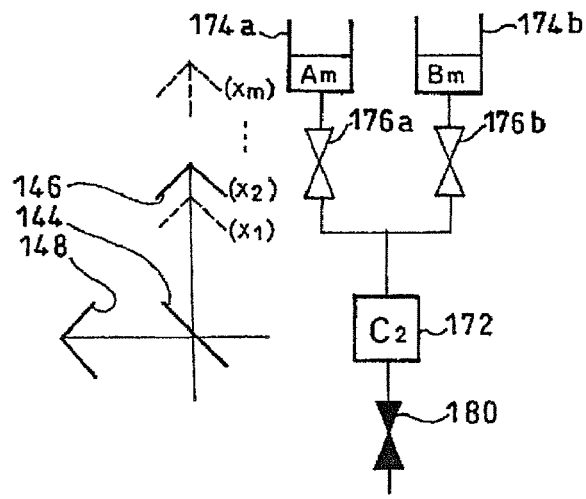
FIG. 6E is a diagram illustrating another step in the irreversible-reaction measurement method according to the second embodiment of the present invention.
Figure 6F:
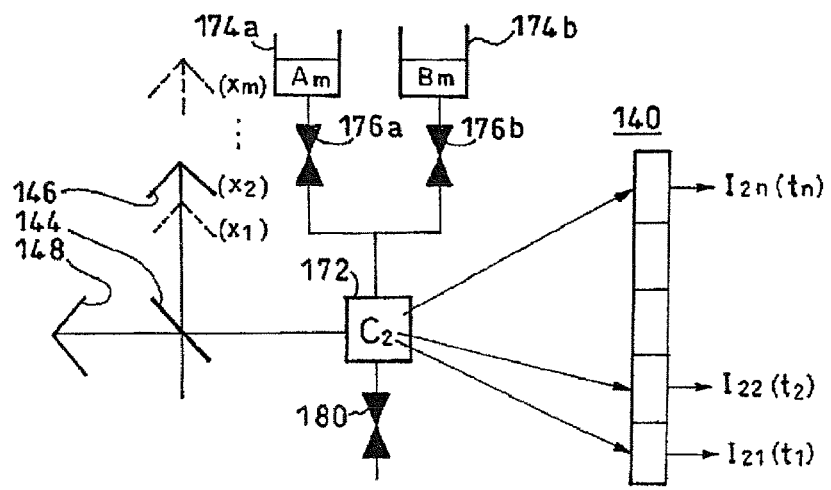
FIG. 6F is a diagram illustrating another step in the irreversible-reaction measurement method according to the second embodiment of the present invention.

Then, after the movable mirror 146 moves to and remains at the next measurement data point $x_2$, as shown in FIG. 6E, the stopped-flow apparatus 170 replaces the liquid mixture in the reaction cell 172 to the next divided liquid mixture $C_2$, thereby causing the divided liquid mixture $C_2$ in the reaction cell 172 to produce the same reaction as produced in the divided liquid mixture $C_1$, as shown in FIG. 6F. The interferogram data is detected from the divided liquid mixture $C_2$ in the same way as from the divided liquid mixture $C_1$.

By repeating those steps until the interferogram data of the divided liquid mixture $C_m$ is obtained, the fast irreversible reaction of the liquid mixture C is measured.

In the second embodiment, each time the movable mirror 146 moves to and remains at the next measurement data point, the stopped-flow apparatus 170 replaces the divided liquid mixture in the reaction cell 172. Therefore, the fast irreversible reaction of the liquid mixture can be measured by using the step-scan method. While the movable mirror 146 remains at the next measurement data point, the stopped-flow apparatus 170 mixes the predetermined amounts of the divided sample liquids $A_i$ and $B_i$, thereby causing an irreversible reaction in the divided liquid mixture $C_i$ in the reaction cell 172; the interferogram data is detected from the divided liquid mixture $C_i$; after the reaction in the divided liquid mixture $C_i$ reaches the end point, the movable mirror 146 moves to and remains at the next measurement data point; the stopped-flow apparatus 170 replaces the divided liquid mixture $C_i$ in the reaction cell 172 with the next divided liquid mixture $C_{i+1}$, thereby causing a reaction in the liquid mixture $C_{i+1}$ in the reaction cell 172 in the same way as in the other divided liquid mixture; and the interferogram data is detected in the same way. By repeating these steps, the fast irreversible reaction of the liquid mixture C is measured.

Like the first embodiment, the second embodiment uses a multi-channel detector 140 as the detector of the Fourier-transfer infrared spectrophotometer, to detect the interferogram data of the divided liquid mixture $C_i$ in the reaction cell 172 in a reduced measurement time.

Modifications

The present invention is not limited to the structures described above, and modifications may be made within the scope of the invention.

For instance, although the measurement range is the infrared range in the structures described above, the present invention is not limited to this range, and another measurement range can be used.

In the structures, information needed to analyze the irreversible reaction of the measurement sample can be obtained by acquiring temporal changes in time-resolved spectrum, temporal changes in light intensity at a specific wave number, and the like, in accordance with the interferogram data obtained by repeating the individual steps of the present invention.

Figure 7A:
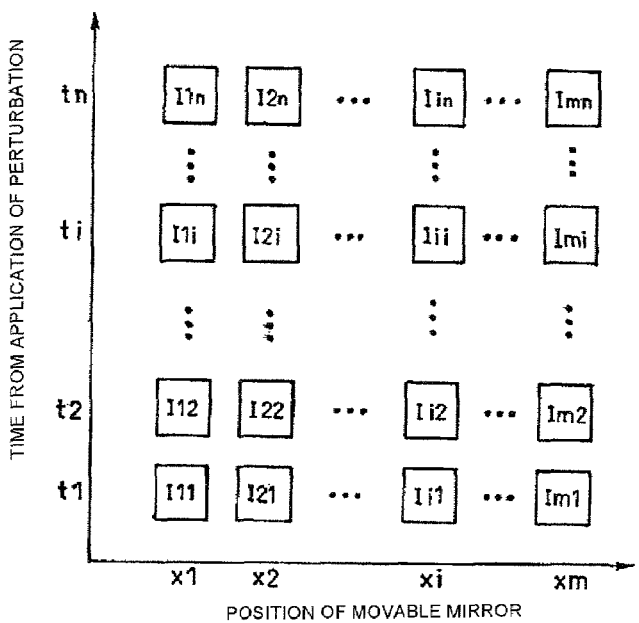
FIGS. 7A to 7C are diagrams illustrating a data processing step in the embodiment.
Figure 7B:
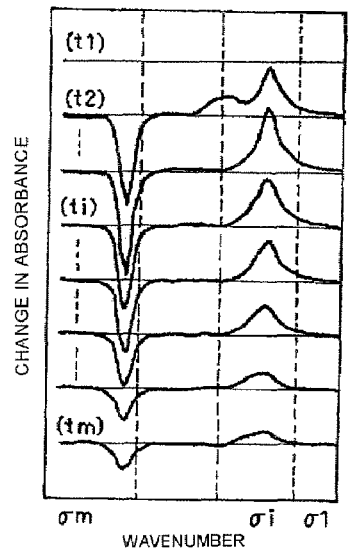
Figure 7C:
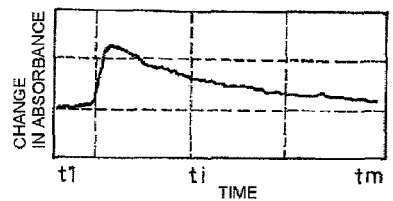

FIG. 7A is a diagram illustrating interferogram data obtained by repeating the individual steps of the present invention. FIG. 7B is a diagram illustrating temporal information of the time-resolved spectrum obtained in accordance with the interferogram data obtained by repeating the individual steps of the present invention. FIG. 7C is a diagram illustrating temporal light intensity information at a specific wave number, obtained in accordance with the interferogram data obtained by repeating the individual steps of the present invention.

In the present invention, after a perturbation is applied as shown in FIG. 7A, the interferogram data $I_{11}$ to $I_{m1}$ at a delay time $t_1$ is Fourier-transformed to obtain spectrum data at the delay time $t_1$. The interferogram data $I_{12}$ to $I_{m2}$ at a delay time $t_2$ after the application of the perturbation is Fourier-transformed to obtain spectrum data at the delay time $t_2$. The spectrum data at a delay time $t_i$ can be obtained by Fourier-transforming the interferogram data $I_{1i}$ to $I_{mi}$ at the delay time $t_i$ after the application of the perturbation. As a result, temporal information of the time-resolved spectrum, as shown in FIG. 7B, can be obtained in the present invention.

In the present invention, the temporal light intensity information at a specific wave number σi corresponding to the position $x_i$ of the movable mirror can be obtained, as shown in FIG. 7C, in accordance with the interferogram data $I_{i1}$ to $I_{in}$ at the position $x_i$ of the movable mirror, shown in FIG. 7A.

What is claimed is:

1. An irreversible-reaction measurement method for measuring an irreversible reaction of a measurement sample, by using a step-scan measurement function of a Fourier-transform spectrophotometer, the measurement sample being divided into a plurality of parts depending on a desired number of measurement data points for the irreversible reaction and measurement thereof, the divided parts of the measurement sample being subjected to similar perturbations and producing similar irreversible reactions, the irreversible reactions in the divided parts of the measurement sample being measured in similar manners, the irreversible-reaction measurement method comprising:

a perturbation-applying step in which a perturbation is applied to one of the divided parts of the measurement sample placed in a measurement light path of the Fourier-transform spectrophotometer to cause an irreversible reaction while a movable mirror of the Fourier-transform spectrophotometer remains at a measurement data point;

a detection step in which interferogram data is detected from the divided part of the measurement sample placed in the measurement light path at predetermined time intervals after the application of the perturbation;

a measurement-data-point setup step in which the movable mirror moves to and remains at the next measurement data point after the reaction of the divided part of the measurement sample placed in the measurement light path reaches an end point;

a sample setup step in which the divided part of the measurement sample placed in the measurement light path is changed to the next divided part of the measurement sample each time the movable mirror moves to the next measurement data point; and a data processing step in which the irreversible reaction of the measurement sample is analyzed in accordance with the interferogram data obtained by repeating the individual steps.

2. An irreversible-reaction measurement method according to claim 1,
wherein the measurement sample is placed on a table, the position of the divided part of the measurement sample in the measurement light path being moved by moving the table;
in the perturbation-applying step, the irreversible reaction is caused by applying a perturbation to the divided part of the measurement sample placed in the measurement light path, among the plurality of divided parts of the measurement sample, which is placed on the table, while the movable mirror is remains at a measurement data point;
in the sample setup step, the divided part of the measurement sample placed in the measurement light path is changed to the next divided part of the measurement sample by moving the table each time the movable mirror moves to the next measurement data point; and
after the reaction of the divided part of the measurement sample placed in the measurement light path reaches the end point, the movable mirror moves to and remains at the next measurement data point, the table is moved to change the divided part of the measurement sample placed in the measurement light path to the next divided part of the measurement sample, a similar perturbation is applied to the next divided part of the measurement sample to cause a similar irreversible reaction, the interferogram data is detected from the next divided part of the measurement sample in a similar way, and this procedure is repeated.

3. An irreversible-reaction measurement method according to claim 1,
wherein the measurement sample is different types of fluids that produce an irreversible reaction when they are mixed in a reaction cell by using a stopped-flow apparatus;
the divided parts of the measurement sample are divided fluids formed by dividing the entire amounts of the different types of fluids into predetermined amounts and mixing them in the reaction cell by using the stopped-flow apparatus;
in the perturbation-applying step, a perturbation is applied to the divided fluid in the reaction cell by mixing the predetermined amounts of the different types of fluids in the reaction cell by means of the stopped-flow apparatus each time the movable mirror moves to the next measurement data point;
in the detection step, the Fourier-transform spectrophotometer is used to detect interferogram data from the divided fluid in the reaction cell each time the movable mirror moves to the next measurement data point;
in the sample setup step, the stopped-flow apparatus is used to replace the divided fluid in the reaction cell each time the movable mirror moves to the next measurement data point; and while the movable mirror remains at the measurement data point, the stopped-flow apparatus is used to mix the predetermined amounts of the different types of fluids in the reaction cell, thereby producing the irreversible reaction in the divided fluid, the interferogram data is detected from the divided fluid, the movable mirror moves to and remains at the next measurement data point after the reaction of the divided fluid reaches the end point, the stopped-flow apparatus is used to replace the divided fluid in the reaction cell with the next divided fluid, thereby producing a similar irreversible reaction in the divided fluid, the interferogram data is detected in a similar way from the divided fluid, and this procedure is repeated.

4. An irreversible-reaction measurement method according to claim 1,
wherein, in the detection step, the interferogram data is detected from the divided part of the measurement sample placed in the measurement light path by a multi-channel detector serving as a detector of the Fourier-transform spectrophotometer; and
the interferogram data of each time period after the application of the perturbation is detected at the measurement data point by scanning the elements of the multi-channel detector successively at regular time intervals after the application of the perturbation to the divided part of the measurement sample placed in the measurement light path while the movable mirror remains at the measurement data point.

5. An irreversible-reaction measurement method according to claim 2,
wherein, in the detection step, the interferogram data is detected from the divided part of the measurement sample placed in the measurement light path by a multi-channel detector serving as a detector of the Fourier-transform spectrophotometer; and
the interferogram data of each time period after the application of the perturbation is detected at the measurement data point by scanning the elements of the multi-channel detector successively at regular time intervals after the application of the perturbation to the divided part of the measurement sample placed in the measurement light path while the movable mirror remains at the measurement data point.

6. An irreversible-reaction measurement method according to claim 3,
wherein, in the detection step, the interferogram data is detected from the divided part of the measurement sample placed in the measurement light path by a multi-channel detector serving as a detector of the Fourier-transform spectrophotometer; and
the interferogram data of each time period after the application of the perturbation is detected at the measurement data point by scanning the elements of the multi-channel detector successively at regular time intervals after the application of the perturbation to the divided part of the measurement sample placed in the measurement light path while the movable mirror remains at the measurement data point.

* * * * *